US008778031B1

(12) United States Patent
Latour, Jr. et al.

(10) Patent No.: US 8,778,031 B1
(45) Date of Patent: Jul. 15, 2014

(54) LIMB PROSTHESIS

(75) Inventors: Robert A. Latour, Jr., Clemson, SC (US); Stephen L. Martin, Seneca, SC (US)

(73) Assignee: Clemson University, Clemson, SC (US)

( * ) Notice: Subject to any disclaimer, the term of this patent is extended or adjusted under 35 U.S.C. 154(b) by 38 days.

(21) Appl. No.: 13/238,857

(22) Filed: Sep. 21, 2011

Related U.S. Application Data

(60) Provisional application No. 61/388,918, filed on Oct. 1, 2010, provisional application No. 61/385,756, filed on Sep. 23, 2010.

(51) Int. Cl.
*A61F 5/01* (2006.01)
*A61H 3/00* (2006.01)

(52) U.S. Cl.
USPC .................. 623/32; 623/27; 623/39; 135/65

(58) Field of Classification Search
USPC .......................... 623/29, 32; 135/65, 68; 602/3
See application file for complete search history.

(56) References Cited

U.S. PATENT DOCUMENTS

| 2,453,742 | A * | 11/1948 | Bowen et al. | 135/77 |
| 6,494,919 | B1 * | 12/2002 | Matthews | 623/32 |
| 6,799,592 | B1 * | 10/2004 | Reynolds | 135/74 |
| 7,303,537 | B1 * | 12/2007 | Snyder et al. | 602/16 |
| 7,600,524 | B2 * | 10/2009 | West | 135/71 |
| 2005/0109379 | A1 * | 5/2005 | Rader | 135/68 |
| 2006/0219280 | A1 * | 10/2006 | Robinson et al. | 135/84 |
| 2007/0251560 | A1 | 11/2007 | Moore | |
| 2010/0130898 | A1 * | 5/2010 | Franke et al. | 602/6 |

* cited by examiner

*Primary Examiner* — David Isabella
*Assistant Examiner* — Dinah Baria
(74) *Attorney, Agent, or Firm* — Dority & Manning, PA

(57) ABSTRACT

Disclosed are limb prostheses for use when normal use of the lower leg is temporarily or permanently lost due to lower leg injury or disease, including below-knee amputation. Disclosed prostheses provide full body weight support and allow a wearer to maintain the use of the hands and arms during ambulation. In addition, a wearer can maintain use of their own knee to flex and extend during ambulation, thereby better controlling the prosthesis during motion and providing a more normal gait as compared to previously known devices. In the event of permanent loss of the lower leg due to below-knee amputation, the disclosed prosthesis provides an alternative to socket-type prosthetic devices.

12 Claims, 9 Drawing Sheets

Side View

Stance Phase

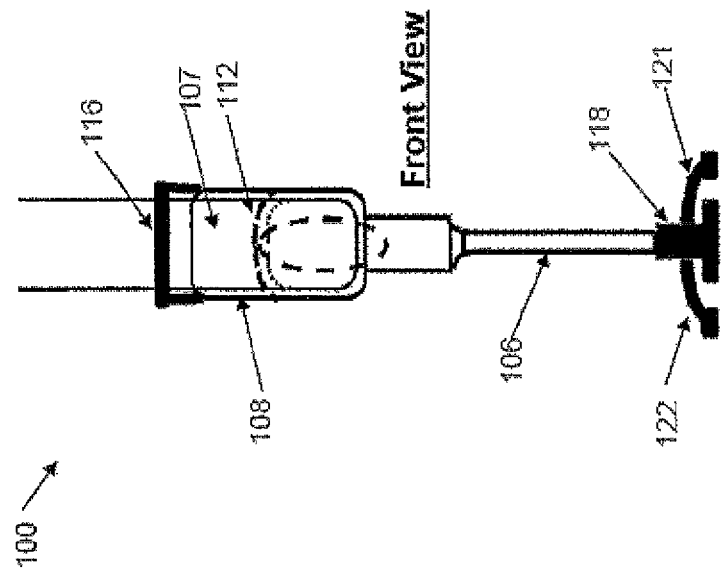
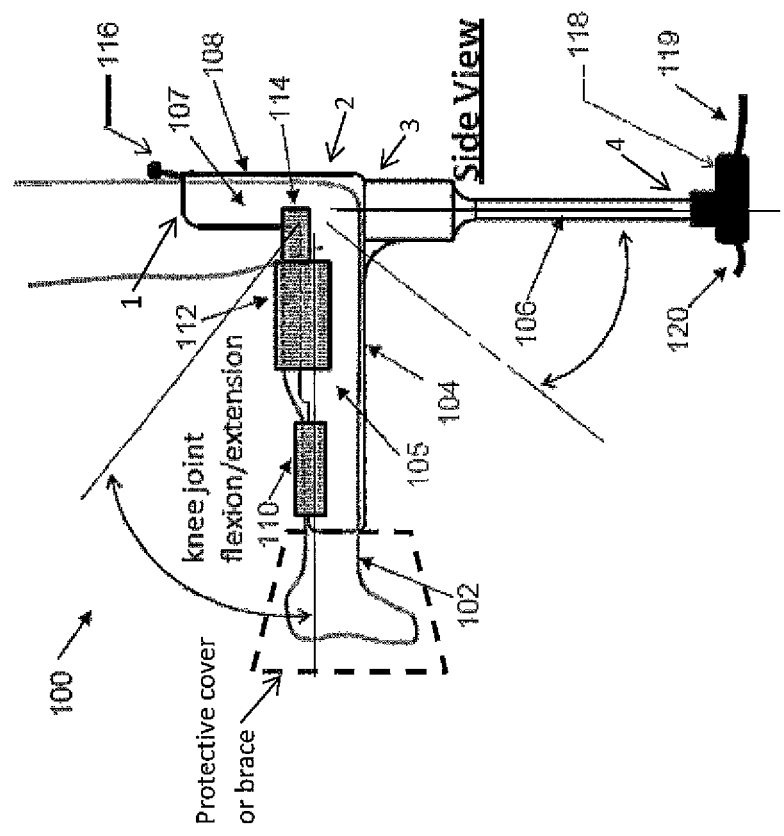
FIG. 1A
FIG. 1B

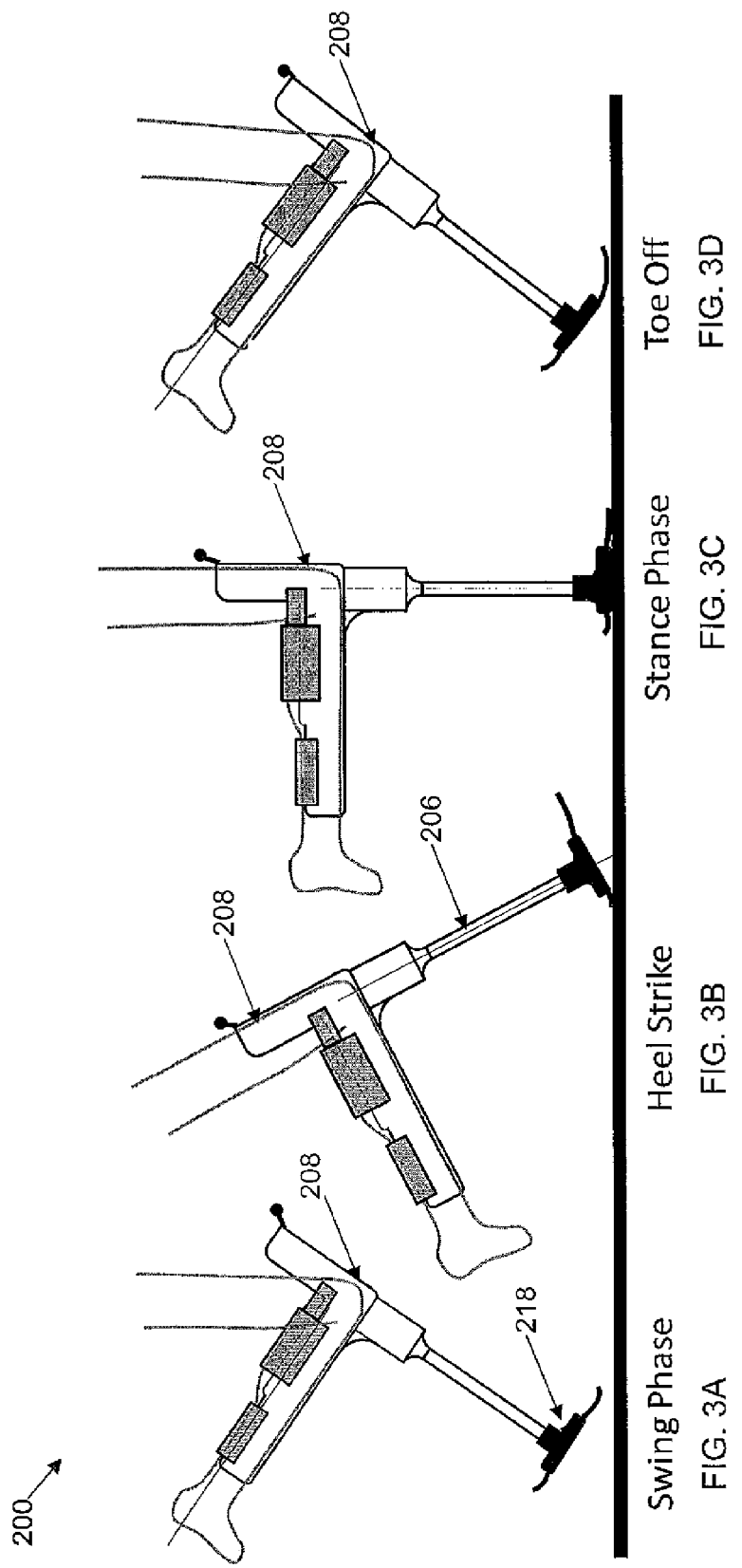

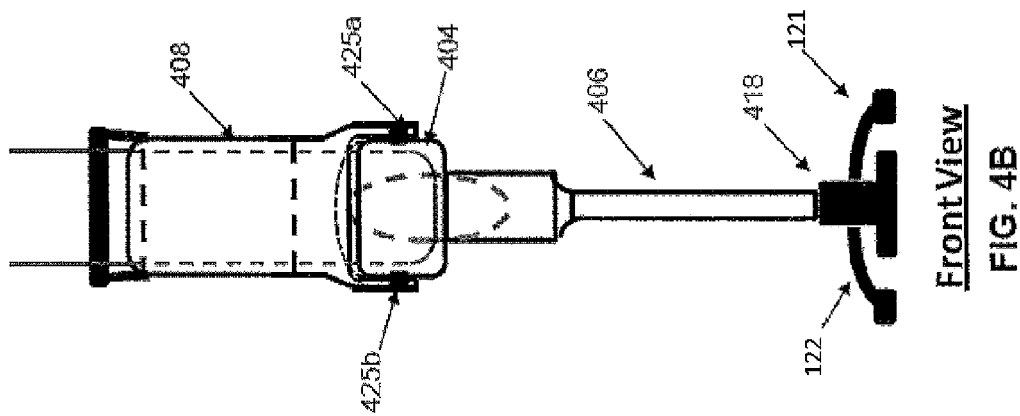
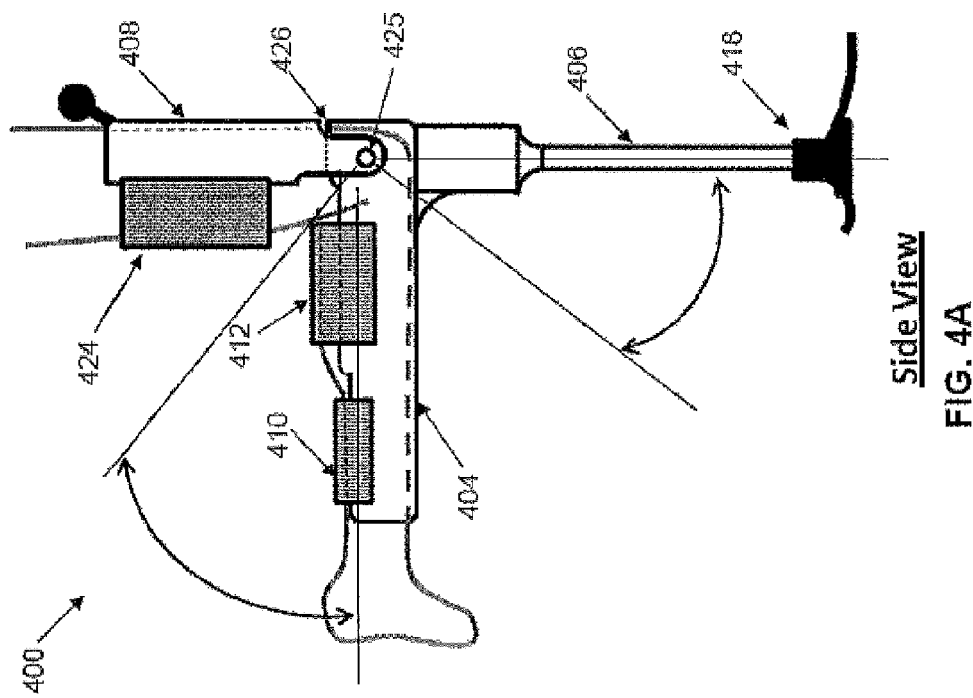
Front View
FIG. 4B
Side View
FIG. 4A

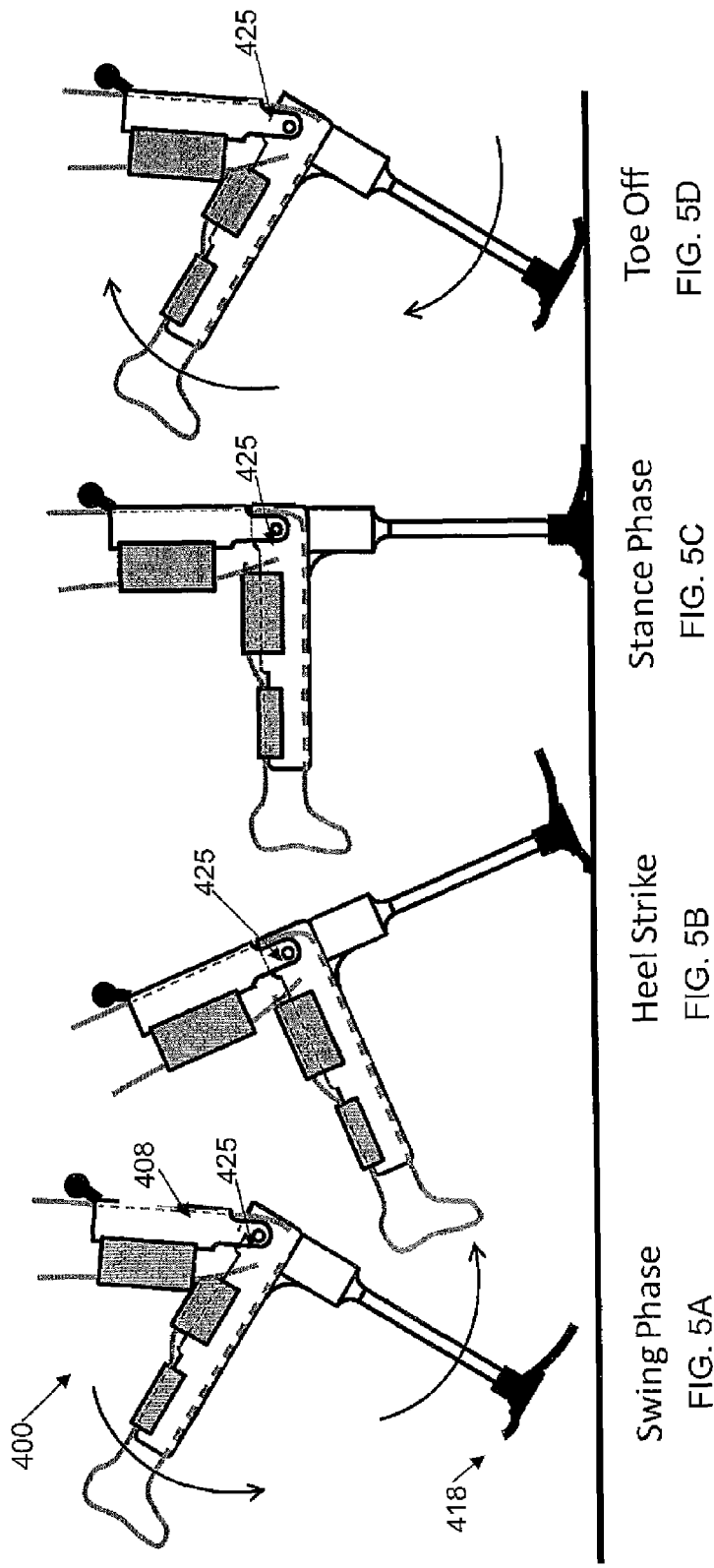

Front View

Side View

LIMB PROSTHESIS

CROSS REFERENCE TO RELATED APPLICATION

This Application claims filing benefit of U.S. Provisional Patent Application Ser. No. 61/385,756 having a filing date of Sep. 23, 2010, and U.S. Provisional Patent Application Ser. No. 61/388,918, having a filing date of Oct. 1, 2010, both of which are incorporated herein by reference.

BACKGROUND OF THE INVENTION

Injury or disease leading to the loss of the use of the lower leg, including soft tissue and bone injury or disease, occur every day and lead to ambulation difficulties for the sufferer. Often, the damage is such that an individual should keep weight and pressure off of the injured limb for several weeks or months. In cases of severe injury or disease (such as diabetes), below-knee amputation may be necessary, in which case the use of the lower limb is permanently lost. Most individuals are able to utilize crutches during the period of rehabilitation, but use of crutches requires a basic level of upper body strength and the contact points between the crutch and the user can develop skin irritation and pain due to pressure. Moreover, a person who also suffers arm or shoulder weakness may need to utilize a wheelchair during rehabilitation.

In the case of below-knee amputation, patients who are not able to comfortably use or afford a socket-type prosthesis permanently need an alternative means of assistance for ambulation. Alternatively, patients who use a socket-type prosthesis may encounter situations when a socket-based prosthesis cannot be worn, such as for a period of time following amputation surgery while the residual limb is healing from the surgery, or when the use of a socket-type prosthesis must be discontinued to provide time to heal from socket-induced pressure sores and/or irritation.

Crutches and wheelchairs both present difficulties for users in navigating doorways, steps, slopes, getting in and out of automobiles, and the like. Crutches also present difficulties due to the loss of the use of the hands and arms, making the carrying of items and other basic functions quite difficult.

Crutchless ambulation devices have been proposed. For instance, U.S. Pat. Nos. 7,303,537, 6,494,919, 6,799,592, 7,600,524, and U.S. Patent Application Publication No. 2007/0251560 describe devices that may be coupled to an individual's leg with the leg held in a flexed position, so as to provide arm free ambulation and support for the injured limb. Unfortunately, such devices prevent any flexion and extension of the knee, leading to an awkward gait for anyone utilizing the devices.

What are needed in the art are limb prostheses for people suffering a lower leg injury or disease that provides for a more natural walking motion. More specifically, what is needed in the art is a limb prosthesis that allows the wearer to use the motion of their own knee to control their motion and maintain the freedom of the arms and hands of the user.

SUMMARY OF THE INVENTION

According to one embodiment, disclosed is a prosthetic device for a lower limb. For instance, the prosthetic device can include an upper portion, a lower leg support, a lower portion, and a prosthetic foot.

The upper portion can have a top 1 and a base 2 that is opposite the top of the upper portion along a longitudinal length of the upper portion. In addition, the upper portion can be free of any attachments for securing the thigh of a wearer to the upper portion.

The lower leg support can extend from the base 2 of the upper portion and can include a proximal end and a distal end, the distal end being opposite the proximal end along a longitudinal length of the lower leg support, and the proximal end being closer to the upper portion than the distal end. The lower leg support can include one or more attachments for securing the lower leg of a wearer to the lower leg support.

The lower portion can extend from the base 2 of the upper portion and can include a top 3 and a base 4 that is opposite the top 3 of the lower portion along a longitudinal length of the lower portion.

The prosthetic foot can be located at the base 4 of the lower portion.

According to another embodiment, disclosed is a prosthetic device that includes an upper portion, a lower leg support, a lower portion, and a prosthetic foot. In this embodiment, the upper portion can include one or more attachments for securing the thigh of a wearer to the upper portion. In addition to the other features, this embodiment of a prosthetic device can include a hinge between the upper portion and the lower leg support, the hinge allowing the upper portion and the lower leg support to flex and extend with respect to one another.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which:

FIG. 1A is a side view of one embodiment of a limb prosthesis as disclosed herein for use by a patient with an intact lower limb.

FIG. 1B is a front view of the limb prosthesis of FIG. 1A.

FIGS. 3A-3D illustrate each phase of a complete step taken utilizing the limb prosthesis of FIG. 2A.

FIG. 4A is a side view of another embodiment of a limb prosthesis as disclosed herein for use by a patient with an intact lower limb.

FIG. 4B is a front view of the limb prosthesis of FIG. 4A.

FIGS. 5A-5D illustrate each phase of a complete step taken utilizing the limb prosthesis of FIG. 4.

Figure 1D:
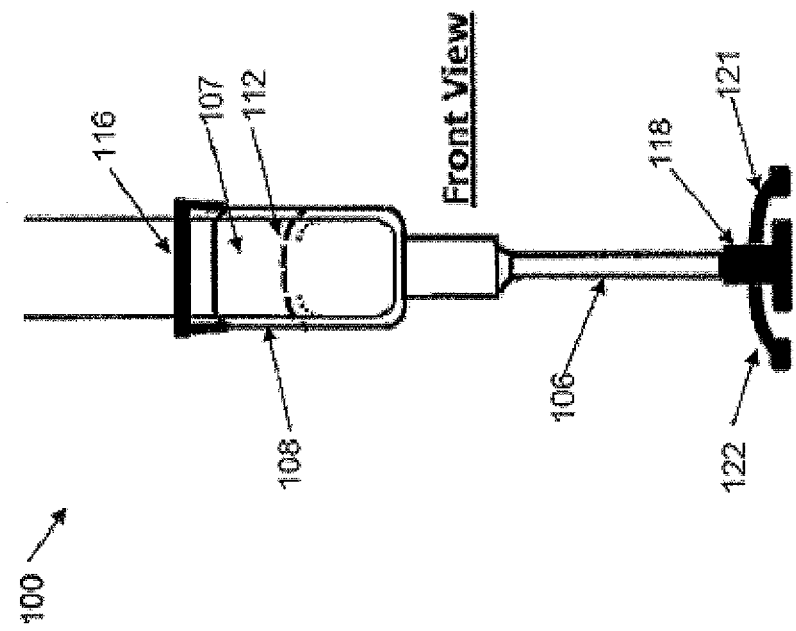
FIG. 1D is a front view of the limb prosthesis of FIG. 10.

Repeat use of reference characters in the present specification and drawings is intended to represent the same or analogous features or elements of the present invention.

DETAILED DESCRIPTION OF REPRESENTATIVE EMBODIMENTS

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment.

Disclosed herein are limb prostheses for use due to a lower leg injury, amputation, or disease. The limb prostheses can be utilized temporarily, for instance during rehabilitation, or can be used permanently, as in the case of amputation. Disclosed prostheses provide full body weight support and allow a wearer to maintain the use of their hands and arms. In addition, a wearer can maintain use of his/her own knee to flex and extend during ambulation, thereby better controlling the prosthesis during motion and providing a more normal gait as compared to previously known devices.

Figure 1C:
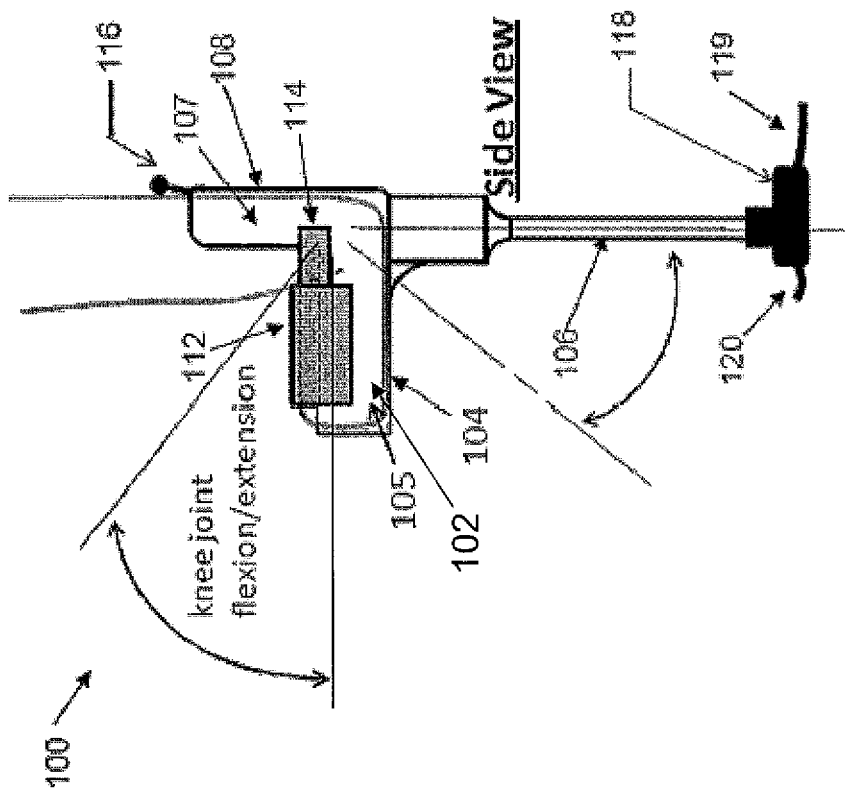
FIG. 1C is a side view of one embodiment of a limb prosthesis as disclosed herein for use by a patient with a below-knee amputation.

FIGS. 1A-1D present side and front views of one embodiment of a limb prosthesis 100. As can be seen, a wearer's lower leg 102 can be supported by prosthesis 100. As shown in FIGS. 1A and 1B, prosthesis 100 can be used during rehabilitation of an injury to the lower leg 102 including both soft tissue and bone injuries during which a patient wishes to ambulate without bearing body weight on the injured lower leg, ankle, or foot. Exemplary injuries include fractures of the foot or ankle (e.g., talus or calcaneous fractures) and/or the distal tibia (e.g., pilon fracture) as well as injuries to ligaments, tendons or muscles, wounds to the foot or toes (e.g., Lacerations or surgical wounds), and so forth. As shown in FIGS. 1C and 1D, prosthesis 100 can be used as an alternative to a socket-type lower-leg prosthesis in the event of below-knee amputation.

In one embodiment, a limb prosthesis can be utilized temporarily following a lower leg amputation surgery, for instance prior to complete healing of an amputation site. The limb prosthesis could provide a route for a patient to become ambulatory prior to healing of the amputation site to the point of supporting a standard prosthesis, a healing process that can take several months. Following complete healing of the amputation site, portions of the limb prosthesis, for instance, lower portion 106 and/or prosthetic foot 118 could be used again in a more permanent prosthetic limb for the patient.

In one embodiment, the limb prosthesis can be used as a permanent ambulation device for individuals with a below-knee amputation, or used as a secondary means of ambulation when an individual has reason to not use a more traditional socket-type prosthesis, such as during healing due to socket-related pressure sores or other forms of irritation.

Prosthesis 100 includes lower leg support 104, upper portion 108 and lower portion 106. Lower leg support 104 can be formed to comfortably fit and hold a length of the lower leg of a wearer. Lower leg support 104 can be of a unitary construction that is sized to fit a wide range of different sized legs, e.g., small, medium, large. Alternatively, lower leg support 104 can be adjustable to provide a more specific sizing capability. For instance, lower leg support can include multiple interconnected components that allow the length of lower leg support 104 (e.g., the distance generally corresponding to the distance from the knee of a wearer to the distal end of the lower leg support 104 near or at the ankle of a wearer or the end of the residual limb in the case of amputation) to be adjusted. Likewise, the cross sectional shape of lower leg support 104 (shown in FIG. 1B, discussed further below) can be adjustable to provide a personalized fit around the calf/leg section of a wearer. In addition, the cross sectional shape of lower leg support 104 can vary along the length of the support. For instance, lower leg support 104 can be tapered so as to be wider at the calf section of the support and narrower at the ankle section of the support.

Lower leg support 104 can include an outer shell 105. Outer shell 105 can be formed of a material such as a moldable plastic or metal, so as to partially encircle a portion of the wearer's lower leg. Lower leg support 104 can also include a material adjacent to the outer shell 105 that will contact the leg of the wearer that can provide improved fit and comfort to a wearer. For instance, inside outer shell 105 of lower leg support 104, a device can include a foam or other cushioning material that can contact and hold the lower leg of a wearer. A contacting material at the inner surface of lower leg support 104 can be moldable so as to more specifically fit the shape of the leg of the wearer, further improving comfort and fit of the prosthetic 100.

In FIG. 1A, the foot of the wearer extends out from the distal end of lower leg support 104. In another embodiment, additional protection can be provided to the ankle and/or foot through inclusion of a protective cover or brace for the wearer. For example, lower leg support 104 can extend and be shaped so as to provide protection to the ankle and/or foot. Alternatively, a prosthetic 100 can include a releasably attachable ankle/foot brace or cover. For instance, an ankle/foot brace can snap or otherwise attach to the distal end of the lower leg support 104. When considering use by patients with a below-knee amputation, additional protection could be provided for the distal end of the residual limb.

Lower leg support 104 also includes attachments 110, 112, 114 for securing the leg of a wearer to the prosthesis 100. Attachments can be adjustable to accommodate a wearer of various leg sizes. For example, attachments 110, 112, 114 can include straps or belts of any convenient width that can wrap the posterior of the lower leg, as shown.

Attachments 110, 112 can be of any suitable size, shape, and number so as to secure the lower leg of a wearer to the lower leg support 104. For example, one, two, three or more individual attachments can be utilized. An attachment 110, 112, can be, for instance, a strap having a width between about 1 and about 9 inches. In one embodiment, a single attachment can overlay a section of the posterior of the lower leg and can secure the lower leg of a wearer to the lower leg support 104. An attachment can use any suitable closure, such as hook and loop style closures, snaps, buckles, ties, clips, etc. as are generally known in the art. An attachment can be a single piece that extends from a first outer edge of the supportive shell 105 of lower leg support 104 and releasably attaches to the opposite outer edge of the supportive shell. Alternatively, an attachment can be a two piece attachment including a first and second section that are affixed to opposite outer edges of the supportive shell 105 and that can be releasable attached to one another, for instance with an adjustable belt clip closure or via a hook and loop type closure.

Attachment 114 is an optional attachment that secures the leg of a wearer to the upper portion 108 of device 100. When included, attachment 114 can be of similar type to attachments 110, 112. However, attachment 114 will not prevent the flexion of the knee of the wearer. Accordingly, attachment 114 will not extend up the posterior of the wearer's leg to any great length and will not be excessively tight.

Upper portion 108 of prosthesis 100 can be formed of a similar material as lower leg support 104. For instance, upper portion 108 can include an outer shell 107 and an inner cushioning material to improve comfort of the device. Additionally, the curvature of upper portion 108 can be fixed or adjustable, as described previously for lower leg support 104. In the embodiment of FIG. 1, upper portion 108 and lower leg support 104 are fixed at an angle of approximately 90° to one another.

Upper portion 108 can partially wrap the thigh of a wearer when standing so as to provide improved stability. Additionally, upper portion can be adjustable in length, so as to extend to any desired height on the thigh of the wearer.

Upper portion 108 may also include a handle 116 that can be located at the front of the device, as shown, or alternatively on either side of the device. Handle 116 can be permanently or removably attached to device 100, and can provide the wearer with additional control during use. For instance, a wearer can use the handle 116 to help in lifting the device, for instance when climbing stairs, or to use the device as a crutch or cane for short distances when the lower leg is not secured to the lower leg support 104 with the attachments 110, 112. A handle 116 can include a formed grip that can be formed of a material such as a metal, ceramic, rubber, a silicone, or a molded thermoset or thermoplastic polymer.

Also included in prosthesis 100 is lower portion 106. Lower portion 106 can be formed of any material that can provide the necessary strength and support to the device. For instance, lower portion 106 can include a reinforced plastic, steel, aluminum, or other metal post that can support the full weight of the wearer during ambulation. Lower portion 106 can generally be adjustable, so as to be properly fitted to the height of the wearer. For instance, a steel shaft of lower portion 106 can include an inner and outer portion that can be moved up and down with relation to one another and can be fixed at a desired height, for instance with a bolt, pin, screw threads, or the like.

At the base of lower portion 106 is a prosthetic foot 118. Prosthetic foot 118 can be similar to known designs of prosthetic feet that are often used for below-the-knee amputee prosthetics. For instance, a prosthetic foot can be hinged or fixed at the ankle, and can generally include a material that will contact the walking surface (e.g., the floor or the ground) that can prevent excessive slippage of the wearer during use, or be covered by a shoe. By way of example, the prosthetic foot 118 can include a natural or synthetic rubber on at least a portion of the base of the prosthetic foot 118.

In one embodiment, prosthetic foot 118 can include a front section 119 and a rear section 120 that can provide shock absorption capability, such as leaf springs, as are generally known in the art. For instance prosthetic foot 118 can simulate both ankle and foot motion at the heel strike and toe-off phases of the gait.

FIG. 1B is a front view of the prosthesis 100 of FIG. 1A. As can be seen, prosthetic foot 118 can include extensions 121, 122, that can provide a broad, self-standing base to the prosthetic foot. Extensions 121, 122 can prevent instability in the foot 118 due to rotation about the long axis of the lower leg support 104. For instance, extensions 121, 122, can extend about two inches or more beyond the width of upper portion 108 to improve side-to-side stability of the prosthetic. Extensions 121, 122 can be permanently affixed to prosthetic foot 118, or can be detachable or retractable, as desired. Optionally, extensions can be adjustable. For instance, extensions 121, 122 can be adjusted to as to rotate and move the distal end of the extension closer to the toe or heel of the prosthetic foot 118. Moreover, the extensions can be adjustable with regard to height from the base of the prosthesis. For example, extensions 121, 122 can rotate upward slightly so as to allow some side to side rotation of the foot 118, but prevent excessive rotation and prevent the wearer from falling.

Figure 2B:
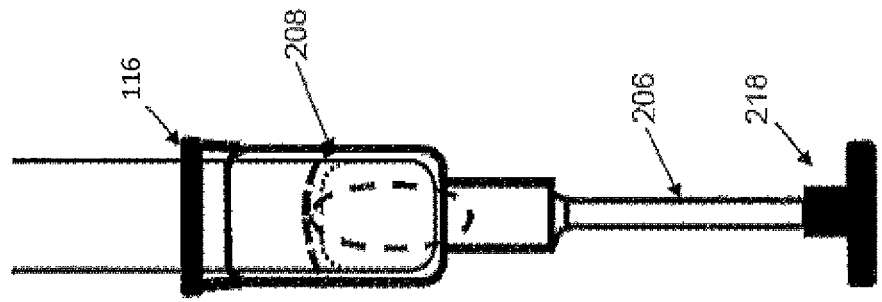
FIG. 2B is a front view of the limb prosthesis of FIG. 2A.
Figure 2A:
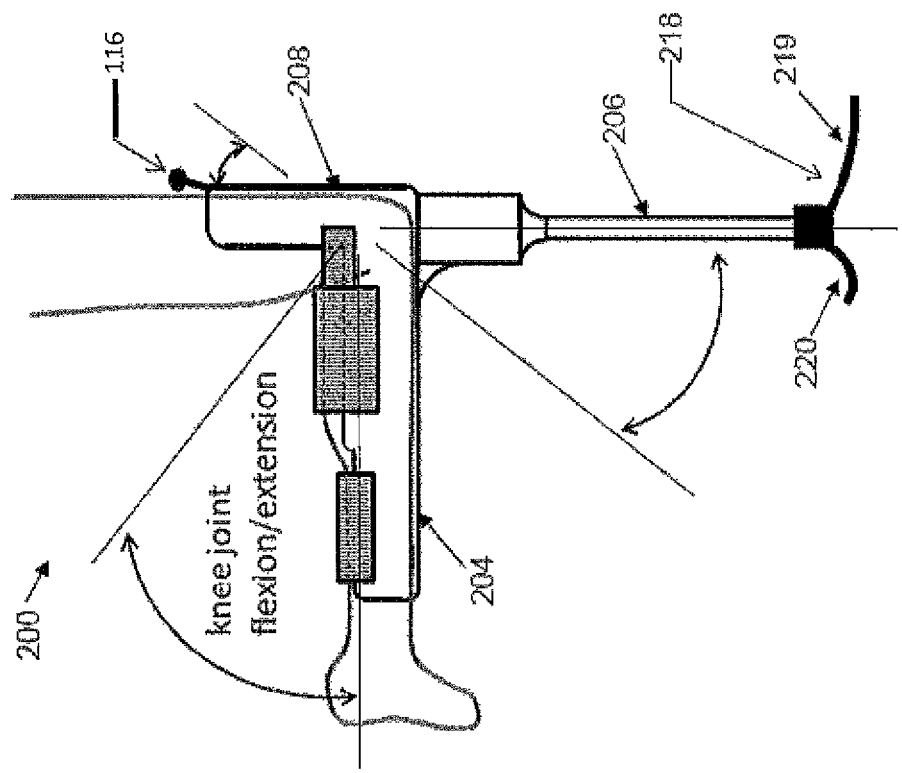
FIG. 2A is a side view of another embodiment of a limb prosthesis as disclosed herein.

It should be understood that there is no particular limitation to the design of the prosthetic foot 118. For instance, FIGS. 2A and 2B illustrate side and front views, respectively, of prosthesis 200. Prosthesis 200 includes a lower leg support 204, an upper portion 208, a lower portion 206, and a foot 218. In addition prosthesis 200 includes attachments for securing the lower leg of a wearer to the prosthesis 200 while allowing the flexion and extension of the knee of the wearer, as described above for prosthesis 100 of FIGS. 1A and 1B. Specifically, the thigh of a wearer is not attached to upper portion 208 so as to prevent the wearer's knee from flexing.

Foot 218 of prosthesis 200 includes front section 219 and rear section 220 that allow some flexibility of the foot 218. For instance, front section 219 and rear section 220 can be leaf springs. As seen in FIG. 2B, prosthesis 200 does not include the side to side extensions as are present in the prosthesis 100 of FIGS. 1A and 1B. Rather, the front section 219 and rear section 220 together are sufficiently wide to provide stability to the prosthesis to help prevent side to side rolling motion of the prosthesis during use.

FIG. 3 illustrates the prosthesis 200 over the course of a single step. In the initial swing phase at FIG. 3A, the wearer's knee is flexed as the prosthetic foot 218 is lifted off of the ground and swung forward by the combined action of the knee and hip joints. The knee of the wearer extends to the point at which the thigh of the wearer strikes the upper portion 208. At the same time the wearer's hip flexes to pull the entire leg forward to the heel strike position (FIG. 3B). The wearer then moves forward through extension at the hip until the foot is flat on the walking surface at the stance phase (FIG. 3C). Finally, the knee of the wearer flexes again away from the upper portion 208 to the toe off phase of the step (FIG. 3D). Throughout the step, the wearer is able to flex and extend both the hip and the knee, which provides better control and a more natural gait to the step as compared to other devices in which flexing and extending of the knee is either prevented or does not impart extension or flexion motion to the lower-limb segment of the prosthesis. Moreover, the design allows for the use of the wearer's own muscles, e.g., the quadriceps, hamstring, etc. to control the step, leading to improved stability and the retention of muscle mass and function.

Figure 4D:
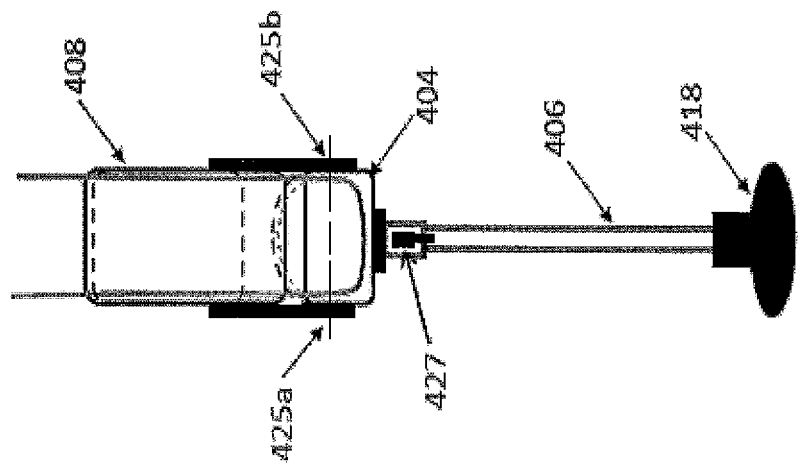
FIG. 4D is a front view of the limb prosthesis of FIG. 4C.
Figure 4C:
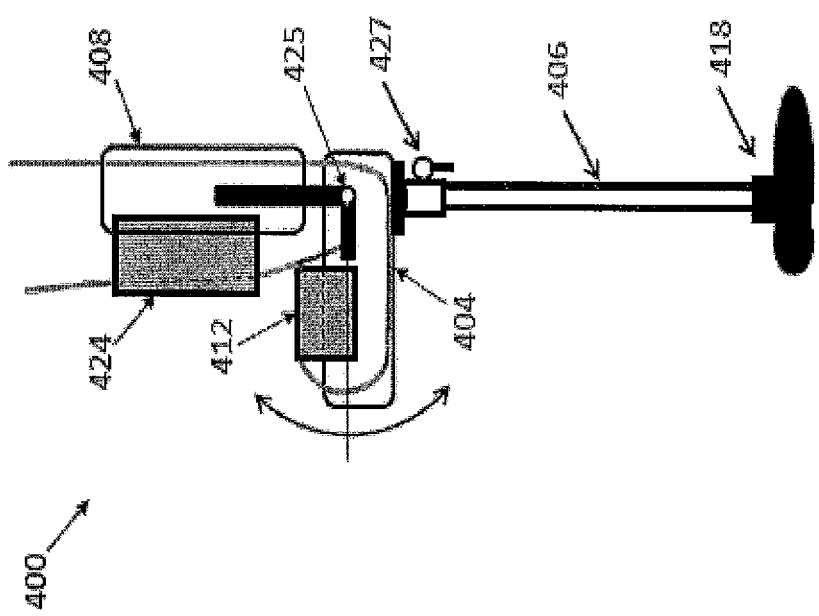
FIG. 4C is a side view of one embodiment of a limb prosthesis for use by a patient with a below-knee amputation.

FIGS. 4A-4D illustrate another embodiment of a prosthetic limb 400 as disclosed herein, which can be used for patients with either lower leg injuries (FIGS. 4A and 4B) or patients with below-knee amputation (FIGS. 4C and 4D). This embodiment, as with the embodiments discussed above, allows the knee of a wearer to flex and extend during use, so as to provide improved stability and a more natural gait to the wearer.

Prosthetic limb 400 includes attachments 410 and/or 412 for attaching the lower leg of a wearer to Lower leg support 404. In addition, prosthetic limb 400 includes an attachment 424 that attaches the wearer's upper leg to upper portion 408. Attachment 424 can include straps, buckles, hook and loop closures, snaps, and the like, as previously described. The attachment of the wearer's upper leg to the upper portion 408 can help prevent side to side rotation around lower leg support 404 of the device during use, thus providing increased stability.

In order to allow the knee of a wearer to flex and extend, prosthetic 400 pivots at a hinge 425 that is located at or near the rotation axis of the knee of the wearer. As shown in FIG. 4B, upper portion 408 and lower leg support 404 can be separate pieces and can be joined with a hinge 425a, 425b at either side of the wearer's knee generally coaxial with the knee's rotational axis. Hinges 425a and 425b can be simple pin hinges, as shown, or can have any other suitable design that can allow the upper portion 408 and the lower leg support 404 to pivot with respect to each other, for instance as exemplified by the two types of designs illustrated in FIGS. 4A and 4C. The lower leg support 404 can include a stop 426 (FIGS. 4A and 4B) that meets upper portion 408 as shown, so as to prevent hyperextension of the prosthetic lower leg compared to the position of the lower leg during normal ambulation. Any suitable mechanism for preventing hyperextension can be utilized, with such mechanism be located on lower leg support 404, on upper portion 408, or as a component of hinge 425.

In one embodiment, the device can be designed without a stop such to allow full extension of the normal knee joint (FIGS. 4C and 4D). Additionally, the hinge can be designed to be able to be locked and unlocked by the user at any desired angle, such as 0° (i.e., full knee extension) or 90° (i.e., 90° knee flexion). For instance, the hinge can include a peg or stop locking mechanism that can be inserted and removed by the user so as to lock the hinge in any desired position.

In one embodiment, the lower portion 406 of the prosthesis can be connected to the lower leg support 404 with a separable connection 427 (FIGS. 4C and 4D), which can be, for example, a quick-connect, a pin joint, or the like. Separable connection 427 can allow a user to remove the lower portion 406 from the rest of the device 400. For instance when a wearer wishes to sit or lay down and wishes to fully extend the leg, removal of the lower portion 406 can be carried out quickly and easily. The lower portion 406 can then be easily reattached to resume ambulation.

As shown in FIGS. 4A and 4C, in one embodiment the hinge 425 of prosthesis 400 can be aligned with the center of lower portion 406 to mimic the alignment of the knee and ankle of a leg, so as to better mimic a natural gait during use.

The upper portion 408 and lower leg support 404 can optionally be of uniform construction, provided that the two sections can allow the wearer's knee to flex and extend as described. For instance, the device can include an extendable portion between the upper portion 408 and the lower leg support 404 that can allow the desired flexing of the prosthesis. An extendable portion can be, for example, an elastic segment.

FIG. 5 illustrates the prosthesis 400 over the course of a single step. In the initial swing phase at FIG. 5A, the wearer's knee is flexed, and the prosthesis 400 is pivoted at the knee hinge 425 as the prosthetic foot 418 is lifted off of the ground while keeping the thigh attached to the upper portion 408 of the prosthesis 400. The knee of the wearer extends along with the upper portion 408 as the foot swings forward. At the same time the wearer's hip flexes to pull the entire leg forward to the heel strike position (FIG. 5B). The wearer then moves forward through extension at the hip until the foot is flat on the walking surface at the stance phase (FIG. 5C). Finally, the knee of the wearer flexes again carrying the upper portion 408 as the hinge 425 pivots to the toe off phase of the step (FIG. 5D). Throughout the step, the wearer is able to flex and extend both the hip and the knee.

Figure 6B:
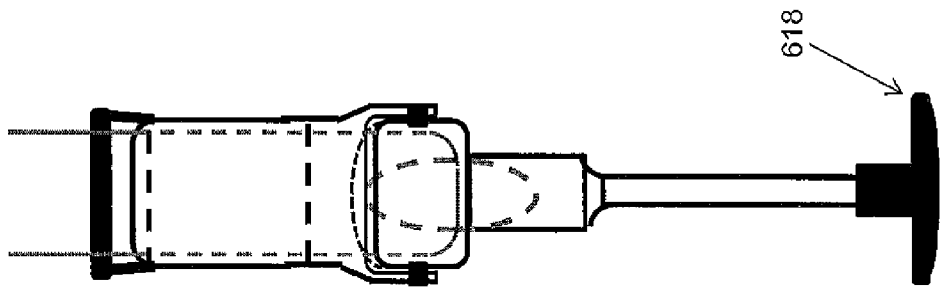
FIG. 6B is a front view of the limb prosthesis of FIG. 6A.
Figure 6A:
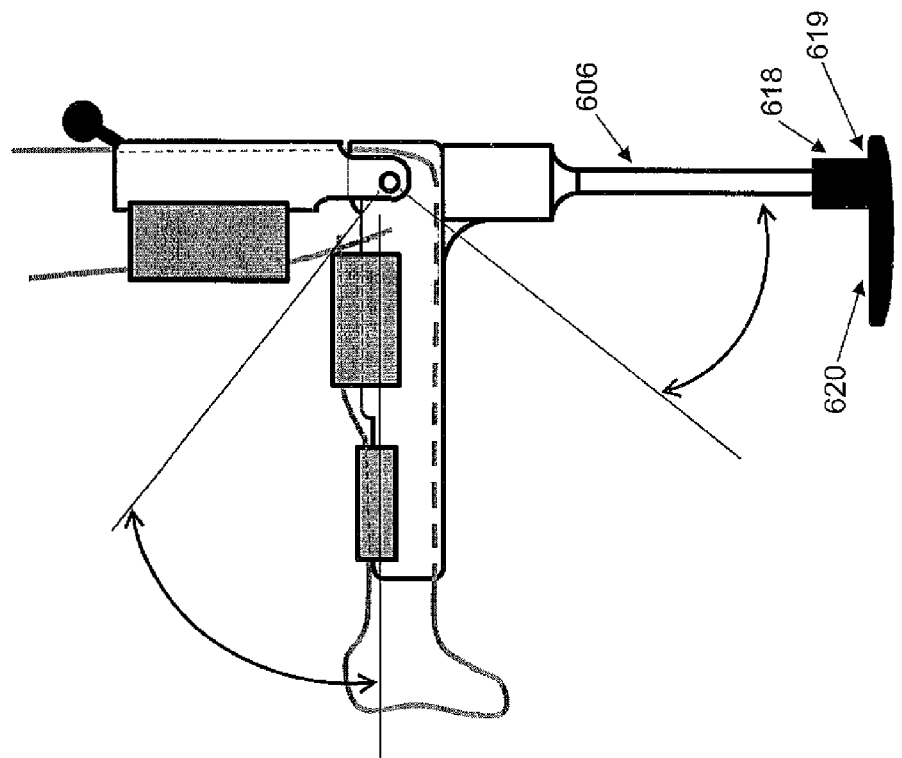
FIG. 6A is a side view of another embodiment of a limb prosthesis as disclosed herein.

FIGS. 6 and 7 illustrate other embodiments of devices that include prosthetic feet 618, 718, as may be utilized in prosthetic devices as described herein. For instance, in the embodiment of FIGS. 6A and 6B, the prosthetic foot 618 includes a back section 620 and a front section 619 that are fixed and are rounded somewhat along the base of the foot 618 to improve a wearer's gait. In addition, the back section 620 is relative long, for instance between about 3 inches and about 5 inches as measured from the center of lower portion 606 to the distal end of the prosthetic foot 618. Additionally, the front section is somewhat short, for instance between about ½ inch and about 2 inches, which, when combined with the slightly rounded base, can provide a toe-off rolling motion to a wearer. In addition, as can be seen in FIG. 6B, prosthetic foot 618 can have a relatively wide side to side base to increase stability of the prosthetic so that it is self-standing when not attached to the leg.

Figure 7B:
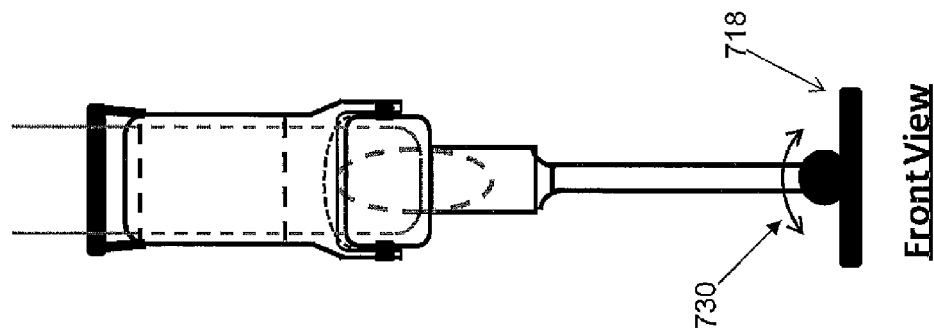
FIG. 7B is a front view of the limb prosthesis of FIG. 7A.
Figure 7A:
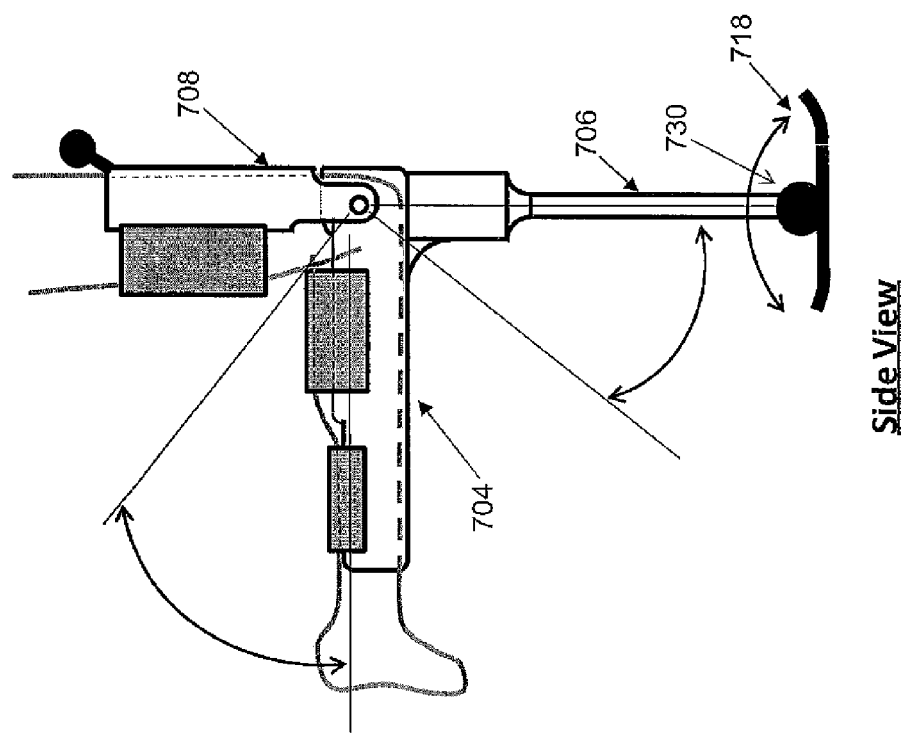
FIG. 7A is a side view of another embodiment of a limb prosthesis as disclosed herein.

The prosthetic foot 718 illustrated in FIGS. 7A and 7B allows for rotation at the joint 730 between lower portion 706 and prosthetic foot 718. In this embodiment, the joint 730 allows both front to back rotation (FIG. 7A) and limited side to side rotation (FIG. 7B), so as to better simulate the range of motion of an ankle. The base of prosthetic foot 718 can also be relatively wide, as shown, to provide stability during use. Prosthetic foot 718 can prove useful on multiple surfaces, for instance on uneven surfaces, due to the ability of the joint 730 to rotate about both the front to back and side-to-side axes. Of course, a prosthetic foot can also be designed to allow rotation about one axis only. For instance, a prosthetic foot can rotate in the front to back (i.e., toe to heel) direction, while preventing rotation in the side to side direction.

It should be understood that any prosthetic foot as is known in the art can be utilized in conjunction with any embodiment of the disclosed prosthetic limbs. For instance, a prosthetic limb as illustrated in FIGS. 4, 5, 6, and 7, in which the wearer's thigh is attached to the upper portion can include a self-standing prosthetic foot including relatively wide extensions, as present in the embodiment illustrated in FIG. 1.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A prosthetic device comprising:
   an upper portion, the upper portion having a top and a base that is opposite the top of the upper portion along a longitudinal length of the upper portion, the upper portion including one or more attachments for securing the thigh of a wearer to the upper portion;
   a lower leg support extending from the base of the upper portion, the lower leg support including a proximal end, the lower leg support including a distal end that is opposite the proximal end along a longitudinal length of the lower leg support, the proximal end being closer to the upper portion than the distal end, the lower leg support including one or more attachments for securing the lower leg of a wearer to the lower leg support;
   a hinge joining the upper portion and the lower leg support, the hinge allowing the upper portion and the lower leg support to flex and extend with respect to one another over the course of a step of a wearer such that an angle between the upper portion and the lower leg support varies during the step of a wearer and may attain a value of less than 90° over the course of the step;
   a lower portion extending from the base of the upper portion, the lower portion including a top and a base that is opposite the top of the lower portion along a longitudinal length of the lower portion; and
   a prosthetic foot at the base of the lower portion, the prosthetic foot being attached to the base of the lower portion at an attachment point; wherein the lower portion has a side view center line, the hinge and the attachment being aligned with this center line such that a side view alignment between the hinge of the device and the attachment point of the prosthetic foot of the device mimics a side view alignment of a natural knee and a natural ankle.

2. The prosthetic device according to claim 1, wherein the lower leg support defines a cross sectional curvature that is tapered from the proximal end to the distal end.

3. The prosthetic device according to claim 1, wherein the lower leg support defines a cross sectional curvature, the lower leg support being adjustable in size in at least one of the longitudinal length of the lower leg support and the cross sectional curvature of the lower leg support.

4. The prosthetic device according to claim 1, further comprising a covering or brace at the distal end of the lower leg support, the covering or brace providing protection to the foot or distal end of the limb of a wearer.

5. The prosthetic device according to claim 4, wherein the covering or brace is releasably attachable to the lower leg support.

6. The prosthetic device according to claim 1, further comprising a handle at the top of the upper portion.

7. The prosthetic device according to claim 1, wherein the lower portion is removably attachable to the upper portion.

8. The prosthetic device according to claim 1, further comprising a rotatable joint between the lower portion and the prosthetic foot.

9. The prosthetic device according to claim 1, wherein at least one of the lower leg support and the upper portion include a cushioning material at a surface.

10. The prosthetic device according to claim 1, wherein the hinge includes a lock.

11. The prosthetic device according to claim 1, wherein the device allows full extension of the knee joint of a wearer.

12. The prosthetic device according to claim 1, wherein the device includes a stop that prevents hyperextension of the lower leg support during ambulation.

* * * * *

UNITED STATES PATENT AND TRADEMARK OFFICE
CERTIFICATE OF CORRECTION

| | | |
|---|---|---|
| PATENT NO. | : 8,778,031 B1 | Page 1 of 1 |
| APPLICATION NO. | : 13/238857 | |
| DATED | : July 15, 2014 | |
| INVENTOR(S) | : Robert A. Latour et al. | |

It is certified that error appears in the above-identified patent and that said Letters Patent is hereby corrected as shown below:

In The Claims

In claim 1, Column 9, Line 2, the word "point" is missing -- "...the attachment point being aligned with this center line such..." --

Signed and Sealed this
Sixth Day of January, 2015

Michelle K. Lee
*Deputy Director of the United States Patent and Trademark Office*